US008206705B2

(12) United States Patent
Rennert et al.

(10) Patent No.: US 8,206,705 B2
(45) Date of Patent: Jun. 26, 2012

(54) KIM-1 ANTIBODIES FOR TREATMENT OF TH2-MEDIATED CONDITIONS

(75) Inventors: Paul Rennert, Holliston, MA (US);
Patricia McCoon, Sudbury, MA (US);
Veronique Bailly, Boxborough, MA (US); Alexey Lugovskoy, Woburn, MA (US)

(73) Assignee: Biogen Idec MA Inc., Cambridge, MA (US)

( * ) Notice: Subject to any disclaimer, the term of this patent is extended or adjusted under 35 U.S.C. 154(b) by 633 days.

(21) Appl. No.: 11/817,638

(22) PCT Filed: Mar. 2, 2006

(86) PCT No.: PCT/US2006/007441
§ 371 (c)(1),
(2), (4) Date: Dec. 22, 2009

(87) PCT Pub. No.: WO2006/094134
PCT Pub. Date: Sep. 8, 2006

(65) Prior Publication Data
US 2010/0150905 A1 Jun. 17, 2010

Related U.S. Application Data

(60) Provisional application No. 60/657,789, filed on Mar. 2, 2005.

(51) Int. Cl.
*A61K 39/395* (2006.01)
(52) U.S. Cl. ............... 424/130.1; 424/133.1; 424/139.1; 424/145.1
(58) Field of Classification Search .................... None
See application file for complete search history.

(56) References Cited

U.S. PATENT DOCUMENTS

| 5,622,861 | A  | 4/1997  | Kaplan et al.       |
|-----------|----|---------|---------------------|
| 6,084,083 | A  | 7/2000  | Levinson            |
| 6,664,385 | B1 | 12/2003 | Sanicola-Nadel et al.|
| 7,041,290 | B2 | 5/2006  | Bailly et al.       |
| 7,179,901 | B2 | 2/2007  | Sanicola-Nadel et al.|
| 7,300,652 | B2 | 11/2007 | Bailly et al.       |
| 7,597,887 | B2 | 10/2009 | Rennert             |
| 7,741,271 | B2 | 6/2010  | Kuchroo et al.      |
| 2003/0124114 | A1 | 7/2003  | McIntire et al.   |
| 2003/0215831 | A1 | 11/2003 | Sanicola-Nadel et al. |
| 2004/0005322 | A1 | 1/2004  | Kuchroo et al.    |
| 2004/0180038 | A1 | 9/2004  | Hancock et al.    |
| 2005/0014687 | A1 | 1/2005  | Anderson et al.   |
| 2005/0089868 | A1 | 4/2005  | Sanicola-Nadel et al. |
| 2005/0095593 | A1 | 5/2005  | McIntire et al.   |
| 2005/0112117 | A1 | 5/2005  | Bailly et al.     |
| 2005/0276756 | A1 | 12/2005 | Hoo et al.        |
| 2006/0222648 | A1 | 10/2006 | Rennert           |
| 2006/0286031 | A1 | 12/2006 | Sanicola-Nadel et al. |
| 2007/0141590 | A1 | 6/2007  | Sanicola-Nadel et al. |
| 2008/0124336 | A1 | 5/2008  | Bailly et al.     |

FOREIGN PATENT DOCUMENTS

| EP | 1062949 | 12/2000 |
| WO | 96/04376 | 2/1996 |
| WO | 97/44459 | 11/1997 |
| WO | 97/44460 | 11/1997 |
| WO | 98/20110 | 5/1998 |
| WO | 98/24804 | 6/1998 |
| WO | 99/37682 | 7/1999 |
| WO | 00/20645 | 4/2000 |
| WO | 01/98481 | 12/2001 |
| WO | 02/098920 | 12/2002 |
| WO | 03/002722 | 1/2003 |
| WO | WO 03/002722 | * 1/2003 |
| WO | 03/025138 | 3/2003 |
| WO | 03/042661 | 5/2003 |
| WO | 03/080856 | 10/2003 |
| WO | 2004/005544 | 1/2004 |
| WO | 2004/060041 | 7/2004 |
| WO | 2004/084823 | 10/2004 |
| WO | 2005/001092 | 1/2005 |

OTHER PUBLICATIONS

Sizing et al. Epitope-dependent effect of anti-murine TIM-1 monoclonal antibodies on T cell activity and lung immune responses. J Immunol. Feb. 15, 2007;178(4):2249-61.*
Sonar et al. Antagonism of TIM-1 blocks the development of disease in a humanized mouse model of allergic asthma. J Clin Invest. Aug. 2, 2010; 120(8): 2767-2781.*
Bailly, V., et al., "Shedding of Kidney Injury Molecule-1, a Putative Adhesion Protein Involved in Renal Regeneration," Journal of Biological Chemistry, (2002) 277(42):39739-39748.
Berg et al., "L-selectin-mediated Lymphocyte Rolling on MadCAM-1," Nature (1993) 366:695-698.
Berlin et al., "alpha-4-beta-7 Integrin Mediates Lymphocyte Binding to the Mucosal Vascular Address in MAdCAM-1," Cell (1993) 74:185-195.
Bonventre and Colvin, "Adhesion Molecules in Renal Disease," Current Opinion in Nephrology and Hypertension (1996) 5:254-261.
Brams, P. et al., "A humanized anti-human CD154 monoclonal antibody blocks CD154-CD40 mediated human B cell activation," International Immunopharmacology Elsevier, Amsterdam, NL (2001), 1(2):277-294.
Briskin et al., "MAdCAM-1 has Homology to Immunoglobulin and Mucin-like Adhesion Receptors and to IgA1," Nature (1993) 363:461-464. Busse W. et al., "Omalizumab, Anti-IGE Recombinant Humanized Monoclonal Antibody, for the Treatment of Severe Allergic Asthma," (2001) *Journal of Allergy and Clinical Immunology*, 108(2):184-190.
Campo CA et al., "Zinc inhibits the mixed lymphocyte culture," Biol. Trace Elem. Res. (2001); 79(1):15-22.
Database Accession No. AC026777, *Homo sapiens* chromosome 5 clone CTC-332D4, complete sequence, retrieved from EMBL, Mar. 27, 2000.
Database Accession No. AL022721, "Human DNA Sequence from clone 109F14 on chromosome 6p21.2-21.3", retrieved from EMBL, Apr. 27, 1998.

(Continued)

*Primary Examiner* — Maher Haddad
(74) *Attorney, Agent, or Firm* — Fish & Richardson P.C.

(57) ABSTRACT

Compositions and methods for treating Th2- and Th1-mediated disease are provided.

37 Claims, 9 Drawing Sheets

OTHER PUBLICATIONS

Database Accession No. AQ277590, "CITBI-E1-2517G14. TFCITBI-E1 *Homo sapiens* genomic clone 2517G14, genomic survey sequence," retrieved from EMBL, Nov. 23, 1998.

Database No. AC005603, *Homo sapiens* subtelomeric cosmid 11b-1, Sep. 3, 1998.

Deng, B. et al., "An Agonist Murine Monoclonal Antibody to the Human c-Mpl Receptor Stimulates Megakaryocytopoiesis," *Blood*, 1998, 92(6):1981-1988.

Dudley et al., "A Requirement for Bone Morphogenetic Protein-7 During Development of the Mammalian Kidney and Eye," Genes & Development (1995) 9:2795-2807.

Encinas et al., "Anti-T-Cell Ig and mucin domain-containing protein 1 antibody decreases $T_H2$ airway inflammation in a mouse model of asthma.", J. of Allergy and Clinical Immunol. (2005), 116(6):1343-1349, (XP002367404).

Fagotto and Gumbiner, "Cell Contact-Dependent Signaling," Developmental Biology (1996) 180:445-454.

Faure et al., "Differentially Expressed Genes in Ischemic Acute Renal Failure", Mol. Biol. Of the Cell, Bethesda, MD, 1998, 9:473A (XP-000953127).

Feigelstock et al., "The human homolog of HAVcr-1 codes for a hepatitis A virus cellular receptor," J. Virol. (1998) 72:6621-6628.

Ferrara et al., "Monoclonal Antibody and Receptor Antagonist Therapy for GVHD.", Cancer Treatment and Research, (1999), 101:331-368.

Gorczynski et al., "A CD200FC Immunoadhesin Prolongs Rat Islet Xenograft Survival in Mice.", Transplantation, Williams and Wilkins, Baltimore, MD, US., (2002), 73(12):1948-1953.

Greve et al., "The Major Human Rhinovirus Receptor Is ICAM-1," Cell (1989) 56:839-847.

Han, W. et al., "Kidney Injury Molecule-1 (KIM-1): A novel biomarker for human renal proximal tubule injury," Kidney International, (2001, 62(1):237-244.

Hoo et al., "Vaccination with Cell Immunoglobulin Mucin-1 Antibodies and Inactivated Influenza Enhances Vaccine-Specific Lymphocyte Proliferation, Interferon-Gamma Production and Cross-Strain reactivity," Clin. Exp. Immunol. (2006); 145(1):123-9.

Hubank and Schatz. "Identifying Differences in mRNA Expression by Representational Difference Analysis of cDNA," Nucleic Acids Research (1994) 22:5640-5648.

Ichimura et al., "Kidney Injury Molecule-1 (KIM-1), a Putative Epithelial Cell Adhesion Molecule . . . ". J. Biol. Chem. 273(7):4135-4142, 1998.

Kalunian K.C. et al., "Treatment of Systemic Lupus Eryheatosus by Inhibition of T cell Costimulation With Anti-CD154," *Arthritis Rheum.* (2002), 46(12): 3251-3258.

Kaplan et al. "Identification of a Surface Glycoprotein on African Green Monkey Kidney Cells as a Receptor for Hepatitis A Virus," EMBO J (1996) 15:4282-96.

Klinken et al, "Mucin Gene Structure and Expression: Protection vs. Adhesion," Am J. Physiol. (1995) 269:G613-G627.

Kuchroo, et al. "The *Tim*Gene Family: Emerging Roles in Immunity and Disease," Nat. Rev. Immunol. (2003) 3:454-62.

Kumanogoh et al. "Class IV semaphorin Sema4A enhances T-cell activation and interacts with Tim-2" Nature (2002) 419:629-33.

Lin G. et al., "Expression of CD34 in endothelial cells, hematopoietic progenitors and nervous cells in fetal and adult mouse tissues" Eur. J. Immunol. (1995) 25:1508-1516.

Luo et al., "BMP-7 is an Inducer of Nephrogenesis and is also Required for Eye Development and Skeletal Patterning," Genes & Development (1995) 9:2808-2820.

McIntire et al. "Identification of *Tapr* (An Airway Hyperreactivity Regulator Locus) and the Linked *Tim*Gene Family," Nat. Immunol. (2001):2:1109-16.

McIntire et al., (2003) *Nature* 425:576.

Monney et al., "Th1-Specific Cell Surface Protein Tim-3 Regulates Macrophage Activation and Severity of an Autoimmune Disease," Nature (2002) 415:536-41.

Moss R.B. et al., "Inhibition of Airway Inflammation by TIM-1 Antibody in a Marine Model of Asthma," (2005) *Journal of Allergy and Clinical Immunology*, 115(4):891.

Muller et al., "Integrin alpha8-beta1 is Critically Important for Epithelial-Mesenchymal Interactions During Kidney Morphogenesis" Cell (1997) 88:603-613.

Owens et al., "The genetic engineering of monoclonal antibodies," J. Immunol. Methods. (1994) 168:149-165.

Padanilam et al., Molecular mechanisms of cell death and regeneration in acute ischemic renal injury, Current Opinion in Nephrology and Hypertension, Rapid Science, London GB 1999, 81(1):15-19 (XP-000953223).

Piccotti Jr., et al., "Interleukin-12 (IL-12)—driven alloimmune," Transplantation (1999); 67(11):1453-60.

Prinz et al., "Treatment of severe cutaneous lupus erythematosus with a chimeric CD4 monoclonal antibody, cM-T412.", J. of the American Academy of Dermatology, (1996), 34:244-52.

Reinsmoen et al., "Evaluation of the Cellular Immune Response in Transplantation," In Manual of Clinical Laboratory Immunology, $6^{th}$ Edition, by Rose, N.R., pp. 1164-1175, (1994).

Rieger et al., Glossary of Genetics. 5th Edition, Springer-Verlag, NY, (1991) 16-17.

Rosenberg et al., "Differential gene expression in the recovery from the ischemic renal injury", Kidney International 39:1156-1161, 1991 (XP-000953186).

Rudikoff et al., "Single amino acid substitution altering antigenbinding specificity," Proc. Nat. Acad. Sci., USA, (1982) 79:1979-1983.

Sastry and Horwitz, "Adhesion-Growth Factor Interactions During Differentiation: An Integrated Biological Response," Developmental Biology (1996) 180:455-467.

Saxena, M. et al., "Inhibition of T cell signaling by mitogen-activated protein kinase-targeted hematopoietic tyrosine phosphatase (HePTO)," The Journal of Biological Chemistry (1999), 274(17):11693-11700.

Shimizu et al., "Mucins in the Mainstream," Nature (1993) 336:630-631.

Shyjan et al., "Human Mucosal Addressin Cell Adhesion Molecule-1 (MAdCAM-1) Demonstrates Structural and Functional Similarities to the alpha-4-beta-7-Integrin Binding Domains of Murine MAdCAM-1," J. of Immunology (1996) 156:2851-2857.

Silberstein et al., "Neutralization of Hepatitis A Virus (HAV) by an Immunoadhesin Containing the Cysteine-Rich Region of HAV Cellular Receptor-1.", J. of Virol. (2001), 75(2):717-725.

Skolnick et al., "From genes to protein structure and function: novel applications of computational approaches in the genomic era," Tibtech (2000) 18:34-39.

Stites et al., Basic and Clinical Immunology, $8^{th}$ edition, pp. 30-31, 208-209, 246-247, (1994).

Takada et al., "The Cytokine-adhesion Molecule Cascade in Ischemia/Reperfusion Injury of the Rat Kidney," J. Clin. Invest. (1997) 99:2682-2690.

Thadhani et al., "Acute Renal Failure," NEJM (1996) 334:1448-1460.

Thompson et al., "The Cys-Rich Region of Hepatitis A Virus Cellular Receptor 1 is Required for Binding of Hepatitis A Virus and Protective Monoclonal Antibody 190/4, "J. of Virology (1998) 72(5):3751-3761.

Totpal, K. et al., "TNF and Its Receptor Antibody Agonist Differ in Mediation of Cellular Responses," *The Journal of Immunology*, 1994, 153(5):2248-2257.

Umetsu Dale, T. et al., "Asthma: an epidemic of dysregulated immunity," Nature Immunology (2002, 3(8):715-720.

Umetsu et al., "TIM-1 Induces T Cell Activation and Inhibits the Development of Pheripheral Tolerance," Nat. Immunol. (2005); 6(5):447-54.

Weterman et al., "nmb, A Novel Gene, is Expressed in Low-Metastatic Human Melanoma Cell Lines and Xenografts," Int. J. Cancer (1995) 60:73-81.

Wills-Karp "Asthma genetics: not for the TIMid?" (2001) Nat Immunol. 2001 2(12):1095-96.

Xia T., et al., "Cimetidine inhibits production of interferon gamma and tumor necrosis factor alpha by splenocytes in aplastic anemic mice," Acta Pharmacologica Sinica (2001), 22(3):239-242.

Xiao et al., "Differential Engagement of Tim-1 During Activation Can positively or Negatively Costimulate T Cell Expansion and Effector Function," J. Exp. Med. (2007); 204(7): 1691-702.

Yung, R., "Etanercept," Current Opinion in Investigational Drugs, Pharmapress, U.S., (2001-02), 2(2):216-221.

Barlow et al., "Tim1 and Tim3 are not essential for experimental allergic asthma," Clinical & Experimental Allergy (2011), pp. 1012-1021.

Degauque et al, "Immunostimulatory Tim-1—specific antibody deprograms Tregs and prevents transplant tolerance in mice," J. Clin. Invest. (2008); 118(2):735-41.

Lin et al., "Are Tim proteins involved in asthma development or pathology?" Clinical & Experimental Allergy (2011), pp. 917-919.

Monoclonal Anti-mouse Tim-1 antibody, Clone 222414, 2005, R&D Systems, Inc.

Toogood et al., "The immune response following small bowel transplantation: I. An unusual pattern of cytokine expression," Transplantation (1996), 62:851-855.

Yuan et al., "Targeting Tim-1 to overcome resistance to transplantation tolerance mediated by CD8 T17 cells," Proc. Nat'l. Acad. Sci U.S.A (2009), 106(26):10734-9.

* cited by examiner

Human KIM-1 amino acid sequence (SEQ ID NO:1):

```
  1  SVKVGGEAGPSVTLPCHYSGAVTSMCWNRGSCSLFTCQNGIVWTNGTHVTYRKDTRYKLL
 61  GDLSRRDVSLTIENTAVSDSGVYCCRVEHRGWFNDMKITVSLEIVPPKVTTTPIVTTVPT
121  VTTVRTSTTVPTTTTVPTTTVPTTMSIPTTTTVPTTMTVSTTTSVPTTTSIPTTTSVPVT
181  TTVSTFVPPMPLPRQNHEPVATSPSSPQPAETHPTTLQGAIRREPTSSPLYSYTTDGNDT
241  VTESSDGLWNNNQTQLFLEHSLLTANTTKGIYAGVCISVLVLLALLGVIIAKKYFFKKEV
301  QQLSVSFSSLQIKALQNAVEKEVQAEDNIYIENSLYATD
```

ITALIC = IgV domain
UNDERLINE = mucin domain
BOLD = stalk domain
DOUBLE UNDERLINE = transmembrane domain
LIGHT SHADED = sequences containing the sialic acid binding motif
DARK SHADED AND UNDERLINED = sequence corresponding to mouse alternatively spliced variant

Fig. 1

SEQUENCE LISTING

```
<160> NUMBER OF SEQ ID NOS: 2

<210> SEQ ID NO 1
<211> LENGTH: 339
<212> TYPE: PRT
<213> ORGANISM: human

<400> SEQUENCE: 1

Ser Val Lys Val Gly Gly Glu Ala Gly Pro Ser Val Thr Leu Pro Cys
1               5                   10                  15

His Tyr Ser Gly Ala Val Thr Ser Met Cys Trp Asn Arg Gly Ser Cys
            20                  25                  30

Ser Leu Phe Thr Cys Gln Asn Gly Ile Val Trp Thr Asn Gly Thr His
        35                  40                  45

Val Thr Tyr Arg Lys Asp Thr Arg Tyr Lys Leu Leu Gly Asp Leu Ser
    50                  55                  60

Arg Arg Asp Val Ser Leu Thr Ile Glu Asn Thr Ala Val Ser Asp Ser
65                  70                  75                  80

Gly Val Tyr Cys Cys Arg Val Glu His Arg Gly Trp Phe Asn Asp Met
                85                  90                  95

Lys Ile Thr Val Ser Leu Glu Ile Val Pro Pro Lys Val Thr Thr Thr
            100                 105                 110

Pro Ile Val Thr Thr Val Pro Thr Val Thr Val Arg Thr Ser Thr
        115                 120                 125

Thr Val Pro Thr Thr Thr Thr Val Pro Thr Thr Thr Val Pro Thr Thr
    130                 135                 140

Met Ser Ile Pro Thr Thr Thr Val Pro Thr Thr Met Thr Val Ser
145                 150                 155                 160

Thr Thr Thr Ser Val Pro Thr Thr Ser Ile Pro Thr Thr Thr Ser
                165                 170                 175
```

```
Val Pro Val Thr Thr Thr Val Ser Thr Phe Val Pro Pro Met Pro Leu
            180             185             190

Pro Arg Gln Asn His Glu Pro Val Ala Thr Ser Pro Ser Ser Pro Gln
            195             200             205

Pro Ala Glu Thr His Pro Thr Thr Leu Gln Gly Ala Ile Arg Arg Glu
            210             215             220

Pro Thr Ser Ser Pro Leu Tyr Ser Tyr Thr Thr Asp Gly Asn Asp Thr
225             230             235             240

Val Thr Glu Ser Ser Asp Gly Leu Trp Asn Asn Asn Gln Thr Gln Leu
                245             250             255

Phe Leu Glu His Ser Leu Leu Thr Ala Asn Thr Thr Lys Gly Ile Tyr
            260             265             270

Ala Gly Val Cys Ile Ser Val Leu Val Leu Leu Ala Leu Leu Gly Val
            275             280             285

Ile Ile Ala Lys Lys Tyr Phe Phe Lys Lys Glu Val Gln Gln Leu Ser
            290             295             300

Val Ser Phe Ser Ser Leu Gln Ile Lys Ala Leu Gln Asn Ala Val Glu
305             310             315             320

Lys Glu Val Gln Ala Glu Asp Asn Ile Tyr Ile Glu Asn Ser Leu Tyr
            325             330             335

Ala Thr Asp

<210> SEQ ID NO 2
<211> LENGTH: 23
<212> TYPE: PRT
<213> ORGANISM: Mus musculus

<400> SEQUENCE: 2

Glu Pro Thr Thr Phe Cys Pro His Glu Thr Thr Ala Glu Val Thr Gly
1               5                   10                  15

Ile Pro Ser His Thr Pro Thr
            20
```

KIM-1 ANTIBODIES FOR TREATMENT OF TH2-MEDIATED CONDITIONS

CROSS REFERENCE TO RELATED APPLICATIONS

This application is a national phase filing under 35 U.S.C. §371 of international application number PCT/US2006/007441, filed Mar. 2, 2006, which claims priority from provisional application No. 60/657,789, filed Mar. 2, 2005. The entire content of each of these prior applications is incorporated herein by reference in its entirety.

BACKGROUND OF THE INVENTION

Atopic diseases such as allergic asthma and atopic dermatitis are thought to involve a pathogenic shift to predominant Th2 immunity (Umetsu et al., 2002, Nat. Immunol. 3:715-20.

In the asthma setting Th2 cytokine production drives eosinophil influx into the lung, eosinophil activation, IgE production and IgE mediated mast cell activation and degranulation, and mononuclear cell accumulation in lung interstitial space, where T cells and activated granulocytes continue to secrete Th2 cytokines, chemokines, and effector molecules, thereby fostering continued lung inflammation. The TAPR locus containing the KIM gene family has been implicated in the development of atopic inflammation in mouse, and KIM-1 allelic variation has been associated with the incidence of atopy in patient population analyses (McIntire et al., 2001, Nat Immunol 2:1109-16; McIntire et al., 2003, Nature 425:576).

SUMMARY OF THE INVENTION

The invention is based, at least in part, on the discovery that agents, such as antibodies, that bind particular regions of KIM-1, can differentially modulate Th1 and/or Th2-mediated immunity. For example, agents that bind the stalk region of KIM-1 or the sialic acid binding regions of KIM-1 can modulate the expression of Th2 cytokines and can be used to treat a Th2 mediated disorder, e.g., asthma; and agents that bind particular epitopes within the mucin region of KIM-1 can reduce a pathogenic Th1 response and can be used to treat a Th1-mediated disorder, e.g., inflammatory disorders or autoimmune disorders such as inflammatory bowel disease (IBD), Crohn's disease, multiple sclerosis, diabetes, rheumatoid arthritis, psoriasis, acute graft versus host disease (GVHD), transplant, pancreatitis, delayed type hypersensitivity (DTH). Compositions and methods useful in the treatment of Th2 and Th1 mediated disorders are provided.

In one aspect, the invention provides methods for treating Th2-mediated conditions, e.g., asthma (particularly allergic asthma), allergic rhinitis, allergy, eczema, and other atopic conditions. The methods include administering to a mammal, preferably a human, having a Th2-mediated condition, an agent that binds the stalk region of KIM-1 or the sialic acid binding motif of KIM-1. For example, the method can include administering a pharmaceutical composition containing a monospecific antibody, e.g., a monoclonal antibody (or antigen-binding fragment thereof) that binds the stalk region of KIM-1 or the sialic acid binding motif of KIM-1, in an amount and for a time sufficient to treat the condition. The stalk region of KIM-1 is identified herein as a charged domain containing highly conserved N-linked glycosylation sites, present between the mucin domain and the transmembrane domain of KIM-1. The stalk region of human KIM-1 and the sialic acid binding motif are shown in FIG. 1. It is understood that the N- and C-termini of these regions as defined herein are approximate and may contain a few (e.g., 1, 2 or 3) more or fewer contiguous residues from the KIM-1 sequence.

In one embodiment, the agent is an antibody that binds to the human KIM-1 stalk region. For example, the antibody binds a peptide having the sequence DGNDTVTESSDGL-WNNNQTQLFLEHSLLTANTTK (amino acids 236-269 of SEQ ID NO:1). In one embodiment, the antibody binds to a peptide having the sequence LLTANTTKG (amino acids 262-270 of SEQ ID NO:1), HSLLTANTTKG (amino acids 260-269 of SEQ ID NO:1), FLEHSLLTANTTKG (amino acids 257-270 of SEQ ID NO:1) or NQTQLFLEHSLLTANT-TKG (amino acids 252-270 of SEQ ID NO:1). In other embodiments, the antibody binds to a peptide having the sequence of amino acid 236-250 or 236-258 of SEQ ID NO:1.

In one embodiment, the antibody binds to the sialic acid binding motif of KIM-1. For example, the antibody binds, at least partly, to an epitope contained within or overlapping a peptide having the sequence GVYCCRVEHRGWFNDM-KITVSLEIVPP (amino acids 81-107 of SEQ ID NO:1) or RGSCSLFTCQNGIV (amino acids 29-42 of SEQ ID NO:1). In one embodiment, the antibody binds reduced and non-reduced protein, i.e., it binds a linear epitope of at least 4, 5, 6, 7, 8, 9, or 10 contiguous amino acid residues of GVYCCRVE-HRGWFNDMKITVSLEIVPP (amino acids 81-107 of SEQ ID NO:1) or RGSCSLFTCQNGIV (amino acids 29-42 of SEQ ID NO:1).

In another embodiment, the antibody binds a structural epitope to which one or both of the sequences GVYCCRVE-HRGWFNDMKITVSLEIVPP (amino acids 81-107 of SEQ ID NO:1) and RGSCSLFTCQNGIV (amino acids 29-42 of SEQ ID NO:1) contribute. In one embodiment, the epitope may be a structural epitope contained in the human KIM-1 sequence corresponding to an 8 kDa TPCK trypsin fragment of recombinant mouse KIM-1 IgV-human IgG1 Fc fusion.

In one embodiment, the antibody interferes with one or more of residues R86, W92, and F93 of SEQ ID NO:1, which are required for sialic acid binding.

While it is understood that the methods described herein are not bound by any particular mechanism or theory, the antibody may have one or more of the following characteristics: (a) it interferes with an interaction of the sialic acid biding motif on the IgV domain of KIM-1 with the carbohydrates displayed on one or more N-glycosylation sites of the stalk region of KIM-1, (b) it binds or sterically hinders one or more N-linked glycosylation sites in the stalk region, (c) it inhibits down-regulation of KIM-1 signaling, (d) it is an agonist antibody, e.g., upon binding it promotes or increases downstream signaling through KIM-1, (e) it blocks multimerization of KIM-1, (f) it binds or sterically hinders interaction of the stalk region with a co-receptor or ligand to disrupt normal function, (g) it interferes with an interaction of the sialic acid biding motif on the IgV domain of KIM-1 with the carbohydrates displayed on one or more O-glycosylation sites of the mucin region adjacent to the stalk region of KIM-1, (h) it alters structural features of the Ig-domain so as to change protein conformation, e.g., by altering or interfering with disulfide or hydrogen bonding, (i) it alters structural or functional features of the KIM-1 Ig-domain so as to change binding to other proteins such as the KIM-1 ligand.

In one embodiment, the antibody does not inhibit shedding of KIM-1 from the cell surface, e.g., it does not inhibit shedding of KIM-1 from 293 Ebna (E293) cells in culture.

In preferred embodiments the antibody is monospecific, e.g., the antibody is a monoclonal antibody, e.g., a humanized or fully human monoclonal antibody or antigen-binding fragment thereof.

In one embodiment, the condition is allergic asthma. In this embodiment, the method optionally also includes identifying a subject who is at risk for, or has, allergic asthma. Optionally, the method also includes evaluating a symptom of asthma in the subject, e.g., IgE levels, airway hyperresponsiveness, coughing, wheezing, chest tightness, dyspnea, airway smooth muscle contraction, bronchial mucus secretion, inflammation, vasodilation, recruitment of inflammatory cells (e.g., neutrophils, monocytes, macrophages, lymphocytes, eosinophils), goblet cell hyperplasia, release of inflammatory mediators by mast cells or migrating inflammatory cells. The evaluation step can be performed before, during and/or after the administration step. The evaluation can be performed by a physician, other health care provider or by the subject. The evaluation can be performed one or more times, e.g., one or more times after administration, e.g., at least twice during a one week, one month, two month, three month, six month period after the administration, or longer.

In a preferred embodiment, the method includes determining whether the administration of the agent (or multiple administrations) reduced the severity or initiation of one or more symptoms of airway disease in the subject.

In some embodiments, the antibody is co-administered with a second agent effective to treat asthma in the subject, e.g., a corticosteroid, bronchodilator, leukotriene modifier, anti-inflammatory agent, anti-IgE agent (e.g., anti-IgE antibody, e.g., omalizumab (Xolair®)). "Co-administered" or "administered in combination" means administration at the same time or within an interval, e.g., a week, such that the effects of the substances on the patient overlap.

In another embodiment, the condition is allergy, e.g., food allergy or seasonal (e.g., pollen) allergy. A diagnosis of allergy may be made by one or more of: administration of an allergen skin test; determination of IgE concentration in serum (e.g., IgE>300 ng/ml); and determination of allergen-specific IgE or IgG antibodies in serum.

The antibody can be administered in one or more of the following periods: prior to an atopic subject's exposure to allergen; after exposure to allergen but prior to the onset of symptoms; at the time of onset of symptoms; after onset of symptoms.

In one embodiment, the agent is administered as a course of treatment, e.g., in periodic administrations of predetermined frequency, e.g., daily, weekly, biweekly or monthly. In some embodiments, an antibody can be administered for a period of time and/or in an amount sufficient to reduce (e.g., to substantially reduce) the frequency or severity of episodes of wheezing, coughing, shortness of breath, or tightness in the chest, e.g., over a period of time, e.g., 3 months, 6 months, a year or more.

In another aspect, the invention provides an isolated antibody, or antigen binding fragment thereof, that specifically binds the stalk region of KIM-1. The antibody does not inhibit shedding of KIM-1 from E293 cells in culture. In one embodiment, the antibody binds to the human KIM-1 stalk region. For example, the antibody binds a peptide having the sequence DGNDTVTESSDGLWNNNQTQLFLEHSLLTANTTK (amino acids 236-269 of SEQ ID NO:1). In one embodiment, the antibody binds to a peptide having the sequence LLTANTTKG (amino acids 262-270 of SEQ ID NO:1), HSLLTANTTKG (amino acids 260-270 of SEQ ID NO:1), FLEHSLLTANTTKG (amino acids 257-270 of SEQ ID NO:1) or NQTQLFLEHSLLTANTTKG (amino acids 252-270 of SEQ ID NO:1). In other embodiments, the antibody binds to a peptide having the sequence of amino acid 241-254, 242-258, 242-255 of SEQ ID NO:1.

In another aspect, the invention provides an isolated antibody, or antigen binding fragment thereof that specifically binds to a sialic acid binding motif of KIM-1. For example, the antibody binds, at least partly, to an epitope contained within or overlapping the peptide having the sequence GVYCCRVEHRGWFNDMKITVSLEIVPP (amino acids 81-107 of SEQ ID NO:1) or RGSCSLFTCQNGIV (amino acids 29-42 of SEQ ID NO:1). In one embodiment, the antibody binds reduced and non-reduced protein, i.e., it binds a linear epitope of at least 4, 5, 6, 7, 8, 9, or 10 contiguous amino acid residues of GVYCCRVEHRGWFNDMKITVSLEIVPP (amino acids 81-107 of SEQ ID NO:1) or RGSCSLFTCQNGIV (amino acids 29-42 of SEQ ID NO:1). In another embodiment, the antibody binds a structural epitope to which one or both of the sequences GVYCCRVEHRGWFNDMKITVSLEIVPP (amino acids 81-107 of SEQ ID NO:1) and RGSCSLFTCQNGIV (amino acids 29-42 of SEQ ID NO:1) contribute. In some embodiments, the epitope is a structural epitope contained in a human KIM-1 region corresponding to an 8 kDa TPCK trypsin fragment of recombinant mouse KIM-1 IgV-human IgG1 Fc fusion. In one embodiment, the antibody interferes with one or more of residues R86, W92, and F93 of SEQ ID NO:1, which are required for sialic acid binding.

The isolated antibody may have one or more of the following characteristics: (a) it interferes with an interaction of the sialic acid biding motif on the IgV domain of KIM-1 with the carbohydrates displayed on one or more N-glycosylation sites of the stalk region of (b) it binds or sterically hinders one or both N-linked glycosylation sites in the stalk region, (c) it inhibits down-regulation of KIM-1 signaling, (d) it is an agonist antibody, e.g., upon binding it promotes or increases downstream signaling through KIM-1, (e) it blocks multimerization of KIM-1, (f) it binds or sterically hinders interaction of the stalk region with a co-receptor or ligand to disrupt normal function, (g) it interferes with an interaction of the sialic acid biding motif on the IgV domain of KIM-1 with the carbohydrates displayed on one or more O-glycosylation sites of the mucin region adjacent to the stalk region of KIM-1, (h) it alters structural features of the Ig-domain so as to change protein conformation, e.g., by altering or interfering with disulfide or hydrogen bonding, (i) it alters structural or functional features of the KIM-1 Ig-domain so as to change binding to other proteins such as the KIM-1 ligand.

In another aspect, the invention features a method of treating a Th1-mediated condition, e.g., a condition characterized by a pathogenic or increased Th1 response. Such conditions include inflammatory and/or autoimmune disorders such as inflammatory bowel disease (IBD), Crohn's disease, multiple sclerosis, diabetes, rheumatoid arthritis, psoriasis, acute graft versus host disease (GVHD)), transplant, pancreatitis, delayed type hypersensitivity (DTH). The method includes administering to a mammal, preferably a human, having a Th1-mediated condition, an agent, e.g., an antibody, that binds an epitope contained in the sequence VATSPSSPQPAETHPTTLQGAIRREPTSSPLYSYTT (residues 200-235 of SEQ ID NO:1). For example, the method can include administering a pharmaceutical composition containing a monospecific antibody, e.g., a monoclonal antibody (or antigen-binding fragment thereof) that binds the specified region of KIM-1, in an amount and for a time sufficient to treat the condition. The specified region of KIM-1 is found in an alternatively spliced variant of KIM-1 in the mouse. It is understood that the N- and C-termini of this region as defined herein are approximate and may contain a few (e.g., 1 or 2) more or fewer contiguous residues from the KIM-1 sequence.

In one embodiment, the antibody binds reduced and non-reduced protein.

In preferred embodiments the antibody is monospecific, e.g., the antibody is a monoclonal antibody, e.g., a humanized or fully human monoclonal antibody or antigen-binding fragment thereof.

In one embodiment, the condition is inflammatory bowel disease (IBD), Chron's disease, rheumatoid arthritis, psoriasis, acute graft versus host disease (GVHD), transplant, pancreatitis, or delayed type hypersensitivity (DTH). The method optionally also includes identifying a subject who is at risk for, or has, any of the listed conditions.

In a preferred embodiment, the method includes determining whether the administration of the agent (or multiple administrations) reduced the severity or initiation of one or more symptoms of the condition the subject.

In some embodiments, the antibody is co-administered with a second agent effective to treat the condition in the subject, e.g., a corticosteroid or other anti-inflammatory agent, DMARD, anti-TNF therapy or anti-CD20 therapy. "Co-administered" or "administered in combination" means administration at the same time or within an interval, e.g., a week, such that the effects of the substances on the patient overlap.

In one embodiment, the agent is administered as a course of treatment, e.g., in periodic administrations of predetermined frequency, e.g., daily, weekly, biweekly or monthly. In some embodiments, an antibody can be administered for a period of time and/or in an amount sufficient to reduce (e.g., to substantially reduce) the frequency or severity of symptoms, e.g., over a period of time, e.g., 3 months, 6 months, a year or more.

As used herein, the terms "to treat," "treating," and "treatment" refer to administering a therapy in an amount, manner, and/or mode effective to improve or ameliorate a symptom or parameter that characterizes a pathological condition; to reduce the severity of a symptom or parameter that characterizes a pathological condition; to prevent, slow or reverse progression of the pathological condition; or to prevent one or more symptom or parameter of the pathological condition.

As used herein, an "agent that binds" a particular domain of KIM-1 refers to any compound that binds to the specified domain with a $K_d$ of less than $10^{-6}$ M. An example of a KIM-1 binding agent is a KIM-1 binding protein, e.g., a KIM-1 binding antibody, preferably a monospecific antibody.

As used herein the terms "sialic-acid binding region", "sialic-acid binding motif", and "required for sialic-acid binding", and variants of those terms, refer to amino acid residues, amino acid sequences, and amino acid secondary or tertiary structures that are similar or homologous to those amino acid residues, amino acid sequences, and amino acid secondary and tertiary structures identified in the family of sialic-acid-binding Ig-like lectins (Siglecs) that are required for carbohydrate binding.

The term "antibody or antigen binding fragment thereof" encompasses proteins that include at least one immunoglobulin variable region, e.g., an amino acid sequence that provides an immunoglobulin variable domain or immunoglobulin variable domain sequence, sufficient to specifically bind an antigen. For example, the term includes an antigen binding protein that has a heavy (H) chain variable region (abbreviated herein as VH), and a light (L) chain variable region (abbreviated herein as VL). In another example, the term includes an antigen binding protein that includes two heavy (H) chain variable regions and two light (L) chain variable regions. The term encompasses antigen-binding fragments of antibodies (e.g., single chain antibodies, Fab fragments, F(ab')2 fragments, Fd fragments, Fv fragments, and dAb fragments) as well as complete antibodies, e.g., intact immunoglobulins of types IgA, IgG, IgE, IgD, IgM (as well as subtypes thereof). The light chains of the immunoglobulin may be of types kappa or lambda. In one embodiment, the antibody is glycosylated. An antibody can be functional for antibody-dependent cytotoxicity and/or complement-mediated cytotoxicity, or may be non-functional for one or both of these activities. The VH and VL regions can be further subdivided into regions of hypervariability, termed "complementarity determining regions" ("CDR"), interspersed with regions that are more conserved, termed "framework regions" (FR). The extent of the FR's and CDR's has been precisely defined (see, Kabat, E. A., et al. (1991) Sequences of Proteins of Immunological Interest, Fifth Edition, US Department of Health and Human Services, NIH Publication No. 91-3242; and Chothia, C. et al. (1987) J. Mol. Biol. 196:901-917). Kabat definitions are used herein. Each VH and VL is typically composed of three CDR's and four FR's, arranged from amino-terminus to carboxyl-terminus in the following order: FR1, CDR1, FR2, CDR2, FR3, CDR3, FR4.

The foregoing summary and the following description are not restrictive of the invention as claimed.

BRIEF DESCRIPTION OF THE FIGURES

FIG. 1 is an annotated polypeptide sequence (SEQ ID NO:1) of human KIM-1 (without the signal sequence and without the insertional polymorphism MTTVP) showing the various domains described herein.

DETAILED DESCRIPTION OF THE INVENTION

Figure 2:
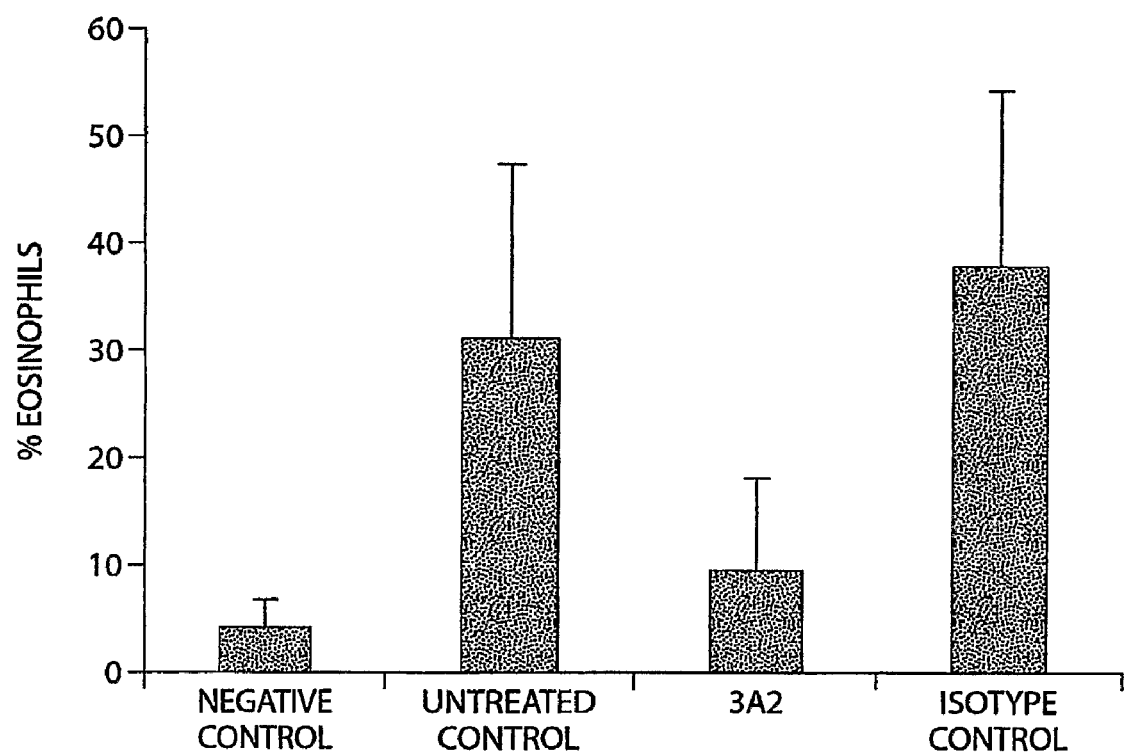
FIG. 2 is a graph showing the percent of eosinophils (y axis) present in bronchial lavage fluid (BAL) after aerosol challenge with OVA and treatment with 3A2.

As described herein, targeting specific regions of KIM-1 with antibody therapy exerts critical control over the expression of Th2 and Th1 cytokines and provides therapeutic strategies for treating Th2 mediated diseases and other atopic disorders, and for Th1 mediated diseases.

Antibody Generation

Antibodies described herein (e.g., antibodies that bind to the stalk region of KIM-1 or to the sialic acid binding motif of KIM-1) can be generated by immunization, e.g., using an animal, or by in vitro methods such as phage display. A polypeptide that includes the target epitope of KIM-1 (e.g., the stalk region of KIM-1 or to the sialic acid binding motif of KIM-1) can be used as an immunogen. In other embodiments, a larger portion of the KIM-1 polypeptide, such as the extracellular domain, can be used as an immunogen and resulting antibodies can be screened for reactivity to the desired KIM-1 region or domain.

In one embodiment, the immunized animal contains immunoglobulin producing cells with natural, human, or partially human immunoglobulin loci. In one embodiment, the non-human animal includes at least a part of a human immunoglobulin gene. For example, it is possible to engineer mouse strains deficient in mouse antibody production with large fragments of the human Ig loci. Using the hybridoma technology, antigen-specific monoclonal antibodies derived from the genes with the desired specificity may be produced and selected. See, e.g., XenoMouse™, Green et al. Nature Genetics 7:13-21 (1994), US 2003-0070185, U.S. Pat. No. 5,789,650, and WO 96/34096.

Non-human antibodies to KIM-1 can also be produced, e.g., in a rodent. The non-human antibody can be humanized, e.g., as described in U.S. Pat. No. 6,602,503, EP 239 400, U.S. Pat. No. 5,693,761, and U.S. Pat. No. 6,407,213.

EP 239 400 (Winter et at) describes altering antibodies by substitution (within a given variable region) of their complementarity determining regions (CDRs) for one species with those from another. CDR-substituted antibodies can be less likely to elicit an immune response in humans compared to true chimeric antibodies because the CDR-substituted antibodies contain considerably less non-human components. (Riechmann et al., 1988, Nature 332, 323-327; Verhoeyen et al., 1988, Science 239, 1534-1536). Typically, CDRs of a murine antibody substituted into the corresponding regions in a human antibody by using recombinant nucleic acid technology to produce sequences encoding the desired substituted antibody. Human constant region gene segments of the desired isotype (usually gamma I for CH and kappa for CL) can be added and the humanized heavy and light chain genes can be co-expressed in mammalian cells to produce soluble humanized antibody.

Queen et al., 1989 and WO 90/07861 have described a process that includes choosing human V framework regions by computer analysis for optimal protein sequence homology to the V region framework of the original murine antibody, and modeling the tertiary structure of the murine V region to visualize framework amino acid residues that are likely to interact with the murine CDRs. These murine amino acid residues are then superimposed on the homologous human framework. See also U.S. Pat. Nos. 5,693,762; 5,693,761; 5,585,089; and 5,530,101. Tempest et al., 1991, Biotechnology 9, 266-271, utilize, as standard, the V region frameworks derived from NEWM and REI heavy and light chains, respectively, for CDR-grafting without radical introduction of mouse residues. An advantage of using the Tempest et al. approach to construct NEWM and REI based humanized antibodies is that the three dimensional structures of NEWM and REI variable regions are known from x-ray crystallography and thus specific interactions between CDRs and V region framework residues can be modeled.

Non-human antibodies can be modified to include substitutions that insert human immunoglobulin sequences, e.g., consensus human amino acid residues at particular positions, e.g., at one or more (preferably at least five, ten, twelve, or all) of the following positions: (in the FR of the variable domain of the light chain) 4L, 35L, 36L, 38L, 43L, 44L, 58L, 46L, 62L, 63L, 64L, 65L, 66L, 67L, 68L, 69L, 70L, 71L, 73L, 85L, 87L, 98L, and/or (in the FR of the variable domain of the heavy chain) 2H, 4H, 24H, 36H, 37H, 39H, 43H, 45H, 49H, 58H, 60H, 67H, 68H, 69H, 70H, 73H, 74H, 75H, 78H, 91H, 92H, 93H, and/or 103H (according to the Kabat numbering). See, e.g., U.S. Pat. No. 6,407,213.

Fully human monoclonal antibodies that bind to desired regions of KM-1 can be produced, e.g., using in vitro-primed human splenocytes, as described by Boerner et al., 1991, J. Immunol., 147, 86-95. They may be prepared by repertoire cloning as described by Persson et al., 1991, Proc. Nat. Acad. Sci. USA, 88: 2432-2436 or by Huang and Stollar, 1991, J. Immunol. Methods 141, 227-236; also U.S. Pat. No. 5,798, 230. Large nonimmunized human phage display libraries may also be used to isolate high affinity antibodies that can be developed as human therapeutics using standard phage technology (see, e.g., Vaughan et al, 1996; Hoogenboom et al. (1998) Immunotechnology 4:1-20; and Hoogenboom et al. (2000) Immunol Today 2:371-8; US 2003-0232333).

As used herein, an "immunoglobulin variable domain sequence" refers to an amino acid sequence that can form the structure of an immunoglobulin variable domain. For example, the sequence may include all or part of the amino acid sequence of a naturally-occurring variable domain. For example, the sequence may omit one, two or more N- or C-terminal amino acids, internal amino acids, may include one or more insertions or additional terminal amino acids, or may include other alterations. In one embodiment, a polypeptide that includes an immunoglobulin variable domain sequence can associate with another immunoglobulin variable domain sequence to form a target binding structure (or "antigen binding site"), e.g., a structure that interacts with a specified region of KIM-1.

The VH or VL chain of the antibody can further include all or part of a heavy or light chain constant region, to thereby form a heavy or light immunoglobulin chain, respectively. In one embodiment, the antibody is a tetramer of two heavy immunoglobulin chains and two light immunoglobulin chains. The heavy and light immunoglobulin chains can be connected by disulfide bonds. The heavy chain constant region typically includes three constant domains, CH1, CH2 and CH3. The light chain constant region typically includes a CL domain. The variable region of the heavy and light chains contains a binding domain that interacts with an antigen. The constant regions of the antibodies typically mediate the binding of the antibody to host tissues or factors, including various cells of the immune system (e.g., effector cells) and the first component (Clq) of the classical complement system.

One or more regions of an antibody can be human, effectively human, or humanized. For example, one or more of the variable regions can be human or effectively human. For example, one or more of the CDRs, e.g., HC CDR1, HC CDR2, HC CDR3, LC CDR1, LC CDR2, and LC CDR3, can be human. Each of the light chain CDRs can be human. HC CDR3 can be human. One or more of the framework regions can be human, e.g., FR1, FR2, FR3, and FR4 of the HC or LC. In one embodiment, all the framework regions are human, e.g., derived from a human somatic cell, e.g., a hematopoietic cell that produces immunoglobulins or a non-hematopoietic cell. In one embodiment, the human sequences are germline sequences, e.g., encoded by a germline nucleic acid. One or more of the constant regions can be human, effectively human, or humanized. In another embodiment, at least 70, 75, 80, 85, 90, 92, 95, or 98% of the framework regions (e.g., FR1, FR2, and FR3, collectively, or FR1, FR2, FR3, and FR4, collectively) or the entire antibody can be human, effectively human, or humanized. For example, FR1, FR2, and FR3 collectively can be at least 70, 75, 80, 85, 90, 92, 95, 98, or 99% identical to a human sequence encoded by a human germline segment.

An "effectively human" immunoglobulin variable region is an immunoglobulin variable region that includes a sufficient number of human framework amino acid positions such that the immunoglobulin variable region does not elicit an immunogenic response in a normal human. An "effectively human" antibody is an antibody that includes a sufficient number of human amino acid positions such that the antibody does not elicit an immunogenic response in a normal human.

A "humanized" immunoglobulin variable region is an immunoglobulin variable region that is modified such that the modified form elicits less of an immune response in a human than does the non-modified form, e.g., is modified to include a sufficient number of human framework amino acid positions such that the immunoglobulin variable region does not elicit an immunogenic response in a normal human. Descriptions of "humanized" immunoglobulins include, for example, U.S. Pat. No. 6,407,213 and U.S. Pat. No. 5,693,762. In some cases, humanized immunoglobulins can include a non-human amino acid at one or more framework amino acid positions.

All or part of an antibody can be encoded by an immunoglobulin gene or a segment thereof. Exemplary human immunoglobulin genes include the kappa, lambda, alpha (IgA1 and IgA2), gamma (IgG1, IgG2, IgG3, IgG4), delta, epsilon and mu constant region genes, as well as the myriad immunoglobulin variable region genes. Full-length immunoglobulin "light chains" (about 25 Kd or 214 amino acids) are encoded by a variable region gene at the NH2-terminus (about 110 amino acids) and a kappa or lambda constant region gene at the COOH-terminus Full-length immunoglobulin "heavy chains" (about 50 Kd or 446 amino acids), are similarly encoded by a variable region gene (about 116 amino acids) and one of the other aforementioned constant region genes, e.g., gamma (encoding about 330 amino acids).

The term "antigen-binding fragment" of a full length antibody refers to one or more fragments of a full-length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) that retains functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., Bird et al. (1988) Science 242:423-426; and Huston et al. (1988) Proc. Natl. Acad. Sci. USA 85:5879-5883.

Antibody Production

Antibodies can be produced in prokaryotic and eukaryotic cells. In one embodiment, the antibodies (e.g., scFv's) are expressed in a yeast cell such as Pichia (see, e.g., Powers et al. (2001) J Immunol Methods. 251:123-35), Hanseula, or Saccharomyces.

In one embodiment, antibodies, particularly full length antibodies, e.g., IgG's, are produced in mammalian cells. Exemplary mammalian host cells for recombinant expression include Chinese Hamster Ovary (CHO cells) (including dhfr-CHO cells, described in Urlaub and Chasin (1980) Proc. Natl. Acad. Sci. USA 77:4216-4220, used with a DHFR selectable marker, e.g., as described in Kaufman and Sharp (1982) Mol. Biol. 159:601-621), lymphocytic cell lines, e.g., NS0 myeloma cells and SP2 cells, COS cells, K562, and a cell from a transgenic animal, e.g., a transgenic mammal. For example, the cell is a mammary epithelial cell.

In addition to the nucleic acid sequence encoding the immunoglobulin domain, the recombinant expression vectors may carry additional nucleic acid sequences, such as sequences that regulate replication of the vector in host cells (e.g., origins of replication) and selectable marker genes. The selectable marker gene facilitates selection of host cells into which the vector has been introduced (see e.g., U.S. Pat. Nos. 4,399,216, 4,634,665 and 5,179,017). Exemplary selectable marker genes include the dihydrofolate reductase (DHFR) gene (for use in dhfr-host cells with methotrexate selection/amplification) and the neo gene (for G418 selection).

In an exemplary system for recombinant expression of an antibody (e.g., a full length antibody or an antigen-binding portion thereof), a recombinant expression vector encoding both the antibody heavy chain and the antibody light chain is introduced into dhfr-CHO cells by calcium phosphate-mediated transfection. Within the recombinant expression vector, the antibody heavy and light chain genes are each operatively linked to enhancer/promoter regulatory elements (e.g., derived from SV40, CMV, adenovirus and the like, such as a CMV enhancer/AdMLP promoter regulatory element or an SV40 enhancer/AdMLP promoter regulatory element) to drive high levels of transcription of the genes. The recombinant expression vector also carries a DHFR gene, which allows for selection of CHO cells that have been transfected with the vector using methotrexate selection/amplification. The selected transformant host cells are cultured to allow for expression of the antibody heavy and light chains and intact antibody is recovered from the culture medium Standard molecular biology techniques are used to prepare the recombinant expression vector, to transfect the host cells, to select for transformants, to culture the host cells, and to recover the antibody from the culture medium. For example, some antibodies can be isolated by affinity chromatography with a Protein A or Protein G.

Antibodies may also include modifications, e.g., modifications that alter Fc function, e.g., to decrease or remove interaction with an Fc receptor or with Clq, or both. For example, the human IgG1 constant region can be mutated at one or more residues, e.g., one or more of residues 234 and 237, e.g., according to the numbering in U.S. Pat. No. 5,648,260. Other exemplary modifications include those described in U.S. Pat. No. 5,648,260.

For some antibodies that include an Fc domain, the antibody production system may be designed to synthesize antibodies in which the Fc region is glycosylated. For example, the Fc domain of IgG molecules is glycosylated at asparagine 297 in the CH2 domain. This asparagine is the site for modification with biantennary-type oligosaccharides. This glycosylation participates in effector functions mediated by Fc receptors and complement Clq (Burton and Woof (1992) Adv. Immunol. 51:1-84; Jefferis et al. (1998) Immunol. Rev. 163: 59-76). The Fc domain can be produced in a mammalian expression system that appropriately glycosylates the residue corresponding to asparagine 297. The Fc domain can also include other eukaryotic post-translational modifications.

Antibodies can also be produced by a transgenic animal. For example, U.S. Pat. No. 5,849,992 describes a method for expressing an antibody in the mammary gland of a transgenic mammal. A transgene is constructed that includes a milk-specific promoter and nucleic acid sequences encoding the antibody of interest, e.g., an antibody described herein, and a signal sequence for secretion. The milk produced by females of such transgenic mammals includes, secreted-therein, the antibody of interest, e.g., an antibody described herein. The antibody can be purified from the milk, or for some applications, used directly.

Antibodies can be modified, e.g., with a moiety that improves its stabilization and/or retention in circulation, e.g., in blood, serum, lymph, bronchoalveolar lavage, or other tissues, e.g., by at least 1.5, 2, 5, 10, or 50 fold.

In one example, a KIM-1 binding antibody can be associated with a polymer, e.g., a substantially non-antigenic polymer, such as a polyalkylene oxide or a polyethylene oxide. Suitable polymers will vary substantially by weight. Polymers having molecular number average weights ranging from about 200 to about 35,000 daltons (or about 1,000 to about 15,000, and 2,000 to about 12,500) can be used.

In another example, a KIM-1 binding antibody can be conjugated to a water soluble polymer, e.g., a hydrophilic polyvinyl polymer, e.g. polyvinylalcohol or polyvinylpyrrolidone. A non-limiting list of such polymers include polyalkylene oxide homopolymers such as polyethylene glycol (PEG) or polypropylene glycols, polyoxyethylenated polyols, copolymers thereof and block copolymers thereof, provided that the water solubility of the block copolymers is maintained. Additional useful polymers include polyoxyalkylenes such as polyoxyethylene, polyoxypropylene, and block copolymers of polyoxyethylene and polyoxypropylene (Pluronics); polymethacrylates; carbomers; branched or unbranched polysaccharides that comprise the saccharide monomers D-mannose, D- and L-galactose, fucose, fructose, D-xylose, L-arabinose, D-glucuronic acid, sialic acid, D-galacturonic acid, D-mannuronic acid (e.g. polymannuronic acid, or alginic acid), D-glucosamine, D-galactosamine, D-glucose and neuraminic acid including homopolysaccharides and heteropolysaccharides such as lactose, amylopectin, starch, hydroxyethyl starch, amylose, dextrane sulfate, dextran, dextrins, glycogen, or the polysaccharide subunit of acid mucopolysaccharides, e.g. hyaluronic acid; polymers of sugar alcohols such as polysorbitol and polymannitol; heparin or heparon.

Uses and Methods of Administration

In the methods described herein, an agent, such as an antibody that binds a particular region of KIM-1, is administered to a subject to treat a Th2-mediated condition or Th1 mediated condition. The subject treated is a mammal, e.g., human.

"Administration" is not limited to any particular formulation, delivery system, or route and may include, for example, intrabronchial, parenteral (including subcutaneous, intravenous, intramedullary, intraarticular, intramuscular, or intraperitoneal injection) rectal, topical, transdermal, or oral (for example, in capsules, suspensions, or tablets). Administration may be provided in a single dose or repeatedly, and in any of a variety of pharmaceutical compositions containing physiologically acceptable salt forms, and/or with an acceptable pharmaceutical excipients. Physiologically acceptable salt forms and pharmaceutical formulations and excipients are known (see, e.g., 2004 Physicians' Desk Reference® (PDR) (2003) Thomson Healthcare, 58th ed; Gennado et al., (2000), 20th ed, Lippincott, Williams & Wilkins) Remington: The Science and Practice of Pharmacy.

A number of therapeutic agents are useful in the management and treatment of asthma. These include, but are not limited to, bronchodilators, e.g., anticholinergic bronchodilators to relax the airway (e.g., ipratropium bromide, albuterol/ipratropium bromide); beta agonists to relax airway muscles (e.g., epinephrine, metaproterenol, terbutaline, isoetharinemesylate, isoetharine, isuprel, pirbuterol, albuterol, salmeterol, bitolterol); oral or inhaled corticosteroids to reduce inflammation (e.g., hydrocortisone, cortisone, dexamethasone, prednisolone, prednisone, methylprednisolone, flunisolide, triamcinolone, beclomethasone, dexamethasone, fluticasone, budesonide); leukotriene modifiers to prevent the airways from swelling and blocking airflow and decrease mucus production (e.g., zafirlukast, montelukast sodium, zileuton); and theophylline, which helps, inter alia, to open the airways and reduce release of phlegm. Anti-asthma agents also include therapeutic antibodies (or functional fragments thereof), including, but not limited to, anti-IgE, anti-IL-9, anti-IL-3, anti-IL-4, anti-IL-5, anti-IL-13, anti-VLA proteins, and anti-migration inhibitory factor (MIF). An antibody described herein can be administered in combination with one or more of the aforementioned agents to treat allergic asthma.

Therapeutic agents are useful in the management and treatment of Th1-mediated inflammatory conditions include anti-inflammatory compounds, e.g., steroids and NSAIDs.

Therapeutically effective dosages achieved in one animal model may be converted for use in another animal, including humans, using known conversion factors (see, e.g., Freireich et al. (1966) Cancer Chemother. Reports, 50(4):219-244.

The following Examples provide illustrative embodiments. The Examples do not in any way limit the invention. One of ordinary skill in the art will recognize numerous modifications and variations that may be performed within the scope of the present invention. Such modifications and variations are therefore encompassed by the invention.

EXAMPLES

Example 1

Characterization of Rat Monoclonal Antibodies to Mouse KIM-1

Using standard PCR and cloning techniques, full-length extracellular domain and IgV domain-only murine KIM-1 expression constructs were generated and stably transfected into CHO cells. These fusion proteins were purified from CHO cell line supernatants by protein-A and SEC chromatography. Full length KIM-1 fused to a human IgG1-Fc domain appeared as a doublet, consistent with differential glycosylation. Rats were immunized with the full-length mouse KIM-1-Ig fusion protein consisting of the entire extracellular domain. A panel of rat monoclonal antibodies to mKIM-1 was identified by ELISA assay and FACS screening, and a set of these were further characterized by Biacore and by domain specific ELISA and Western blot analysis, which demonstrated that multiple antibodies binding distinct epitopes were represented in the panel. Thus, 7 antibodies bound full-length protein in Biacore and ELISA analyses, while 4 of these 7 failed to bind to a protein encoding the IgV-domain only (Table 1). Of the 4 antibodies which appeared to require the presence of the mucin-stalk domains to bind in the Biacore format, 3 were further defined by ELISA and Western blot analysis to bind within the mucin domain, while 1 bound in the stalk domain (Table 1). Within the mucin domain several antibodies recognized a distinct region encoded by exon 4 (Table 1). Thus, antibodies recognizing the IgV, mucin, and stalk domains were identified. Table 1 shows results of gross epitope mapping of the rat-anti-mKIM-1 mAbs. Table 1 data was compiled from multiple assays (Biacore, ELISA, Western blot, and FACS) using the full ECD of KIM-1-Ig, KIM-1-IgV-Ig, and proteolytic fragments of KIM-1-Ig protein.

TABLE 1

|      | ECD domain | IgV domain | ECD minus region encoded by alternatively spliced exon | stalk only |
|------|------------|------------|--------------------------------------------------------|------------|
| 1H9  | +          | +          | +                                                      | −          |
| 1D9  | +          | −          | −                                                      | −          |
| 1C11 | +          | −          | −                                                      | −          |
| 3A2  | +          | −          | +                                                      | +          |
| 1H8  | +          | −          | −                                                      | −          |
| 4A2  | +          | +          | +                                                      | −*         |
| 2A7  | +          | +          | +                                                      | −*         |

*predicted

Example 2

Induction of KIM-1 Expression in Hyperactive Lung

Balb/c mice were primed with OVA/alum twice, then rested for 3 weeks, at which time the mice received 3 days of exposure to OVA aerosol using a nebulizer. Lung tissue, draining (bronchial) lymph node and spleen were harvested and examined for induction of KIM-1 expression by RT-PCR. KIM-1 message was induced in both bronchial LN and lung tissue by 24 hours post nebulization. In contrast to KIM-1 mRNA levels, KIM-3 mRNA levels were not modulated after challenge with OVA aerosol. KIM-2 levels were upregulated in a manner similar to KIM-1.

Example 3

Effect of Anti-KIM-1 Antibodies on OVA-Induced Hyper-Responsiveness

Anti-KIM-1 antibodies with different epitope specificities were tested for the ability to influence the development of lung inflammation using the OVA aerosol model, and using both prophylactic and therapeutic dosing regimens.

For prophylactic studies, OVA-induced lung inflammation and recall assays were performed as follows: Balb/c mice were given ip injections of 100 µl 0.5 mg/ml OVA (Grade V, Sigma) mixed with 100 µl ImjectAlum (Pierce, Rockford Ill. USA) on days 1 and 7. Three weeks after the second injection, mice were exposed for 20 minutes daily for 3 days to an aerosol of 1% OVA in PBS using an ultrasonic nebulizer (Devilbiss, Carlsbad Calif. USA). Dosing with mAbs was as follows: 200 µg was given ip on days 1, 3, 6, and 9, and then 500 µg was given ip the day that nebulizations began.

For therapeutic studies, mice were immunized with OVA in alum as described above, but no mAb was administered until just prior to the nebulization series: thus 250 µg of mAb 4A2 was given the day prior to the first nebulization, and 250 µg of mAb 4A2 was given the morning of the second nebulization.

In both prophylactic and therapeutic studies, two days after the final nebulization session, the mice were sacrificed for analysis. Bronchial lavage fluid (BAL) was collected via tracheotomy using 3 washes with PBS containing 0.1% BSA and 0.02 mM EDTA. BAL cells were pelleted using a cytospin and coated slides (Shandon, Pittsburgh, Pa. USA) then air dried and stained with Hema3 stain (Fisher Scientific, Pittsburgh Pa. USA) for identification of different cell populations. The lung tissue was harvested into neutral buffered formalin for routine histology, or was snap-frozen in trizol for subsequent RNA isolation. Draining (bronchial) lymph nodes and the spleen were harvested for isolation of mononuclear cells, which were placed into culture in RPMI/10% FBS with varying concentrations of OVA. 72 hours later the supernatants were harvested and cells were pulsed for 8 hours with 1 uCi tritiated thymidine (Amersham Biosciences, Piscataway, N.J. USA) and the plates were counted using the Microbetajet system (Wallac, Gaithersburg, Md. USA). Supernatants were analyzed using CBA Th1/Th2 and Inflammation kits (BD Biosciences) and IL-13 ELISA assays (R&D Systems, Minneapolis Minn. USA).

Results:

Mice were dosed with antibodies during the OVA priming and challenge phases. Post challenge, bronchial lavage fluid (BAL), bronchial lymph node, spleen, and lung tissue were harvested. The percent eosinophils, neutrophils, and lymphocytes present in BAL were calculated. mAb 1H8 induced robust eosinophil counts in the BAL of treated mice, such that the percent eosinophils present more than doubled as compared to control. Modest increases in the percent of neutrophils and lymphocytes, which constitute a small fraction of BAL cellularity, were also noted. Consistent with this result, bronchial LN cells isolated from 1H8 treated mice and challenged with OVA ex vivo proliferated more, and expressed higher levels of Th2 associated cytokines than did control cultures. In particular, very high levels of IL-5 and IL-13 were produced, as compared to controls, although levels of IL-4, IL-6, and IL-10 were also elevated. Of interest, IFN-gamma levels were also increased, although overall, levels of this cytokine were low. Preferential induction of Th2 cytokines would be efficacious in settings of Th1 cytokine dependent pathology, such as MS, RA, Crohn's.

Figure 3:
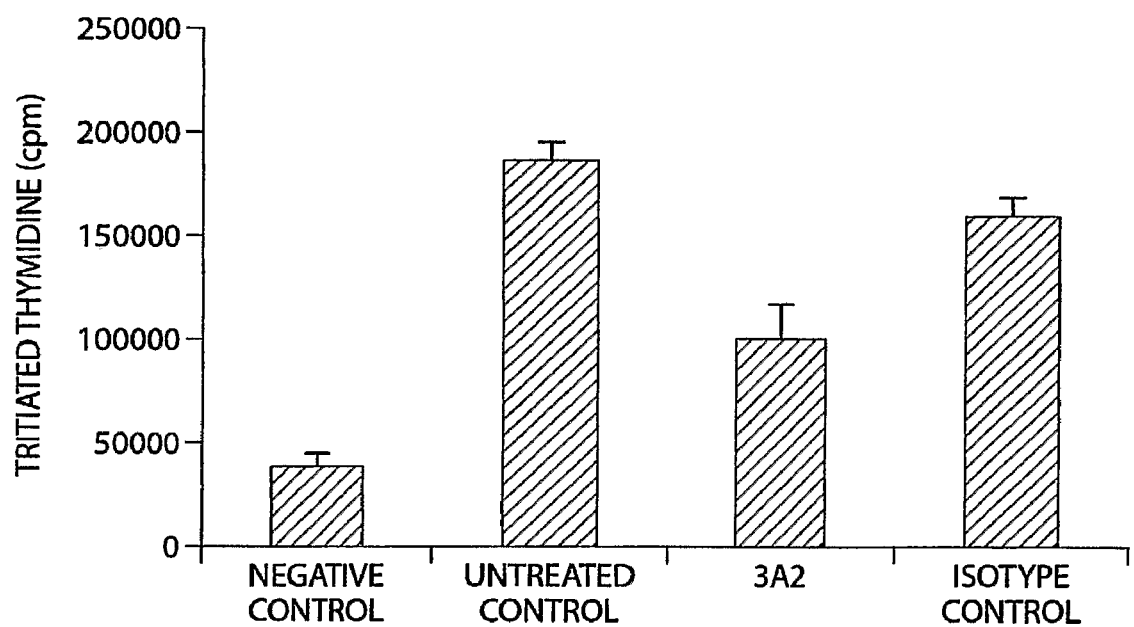
FIG. 3 is a graph showing the proliferation of draining (bronchial) lymph node cells after stimulation ex vivo with the OVA antigen and treatment with 3A2. Y-axis is tritiated thymidine incorporation in cpm.
Figure 4:
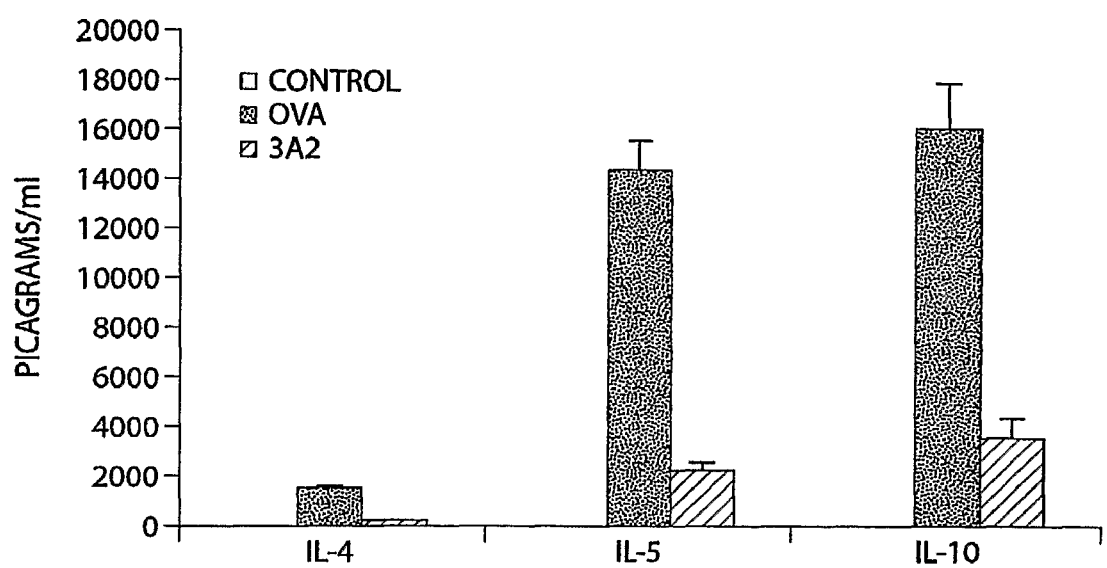
FIG. 4 is a graph showing the response of draining (bronchial) lymph node cells to stimulation ex vivo with the OVA antigen. LN were harvested after OVA aerosol challenge, and then cultured with OVA ex vivo and treatment with 3A2. Supernatants were taken from these cultures and analyzed for TH2 cytokine (IL-4, IL-5 and IL-10) production. Y-axis is picograms/ml.

In contrast with 1H8, mAb 3A2 reduced the percentage of eosinophils in the BAL, and reduced production of Th2-associated cytokines in the bronchial lymph node recall assay (FIG. 2). Thus, the antibodies 1H8 and 3A2 have opposing effects in this assay. Several other antibodies, including 1H9, which recognizes an epitope within the IgV domain, had no effect on lung inflammation or cytokine production in this model. Analysis of the response of draining (bronchial) lymph node cells to stimulation ex vivo with the OVA antigen with 3A2 showed a reduction in the proliferation of cells to antigen stimulation (FIG. 3). Furthermore, the analysis of the supernatants from these cultures showed a marked reduction in the expression of Th2 cytokines including IL-4, IL-5, and IL-10 (FIG. 4). Levels of IL-13 were also reduced in this assay.

Figure 6:
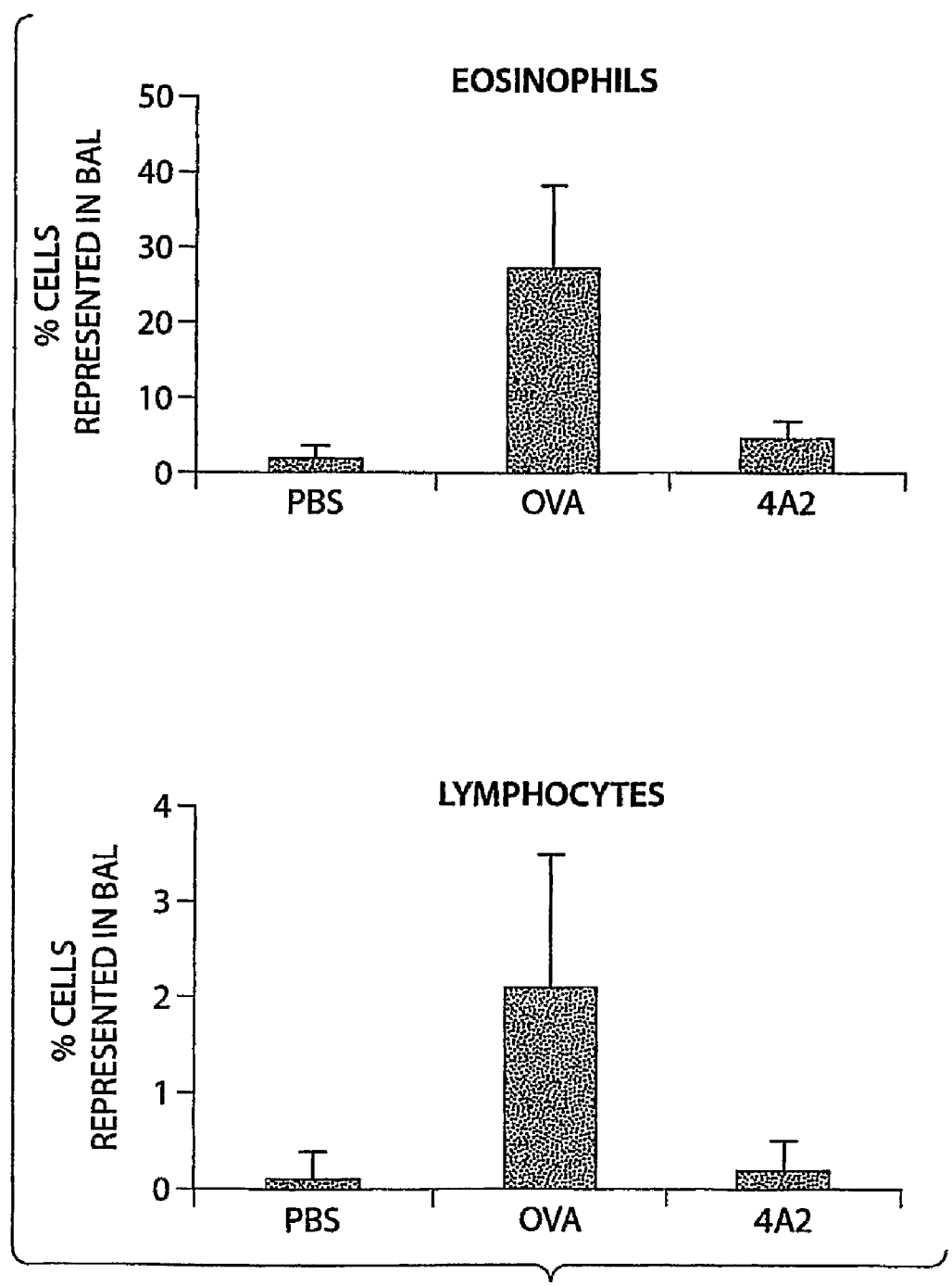
FIG. 6 is a graph showing the percent of eosinophils and lymphocytes (y axes) present in bronchial lavage fluid (BAL) after aerosol challenge with OVA and treatment with 4A2.
Figure 7:
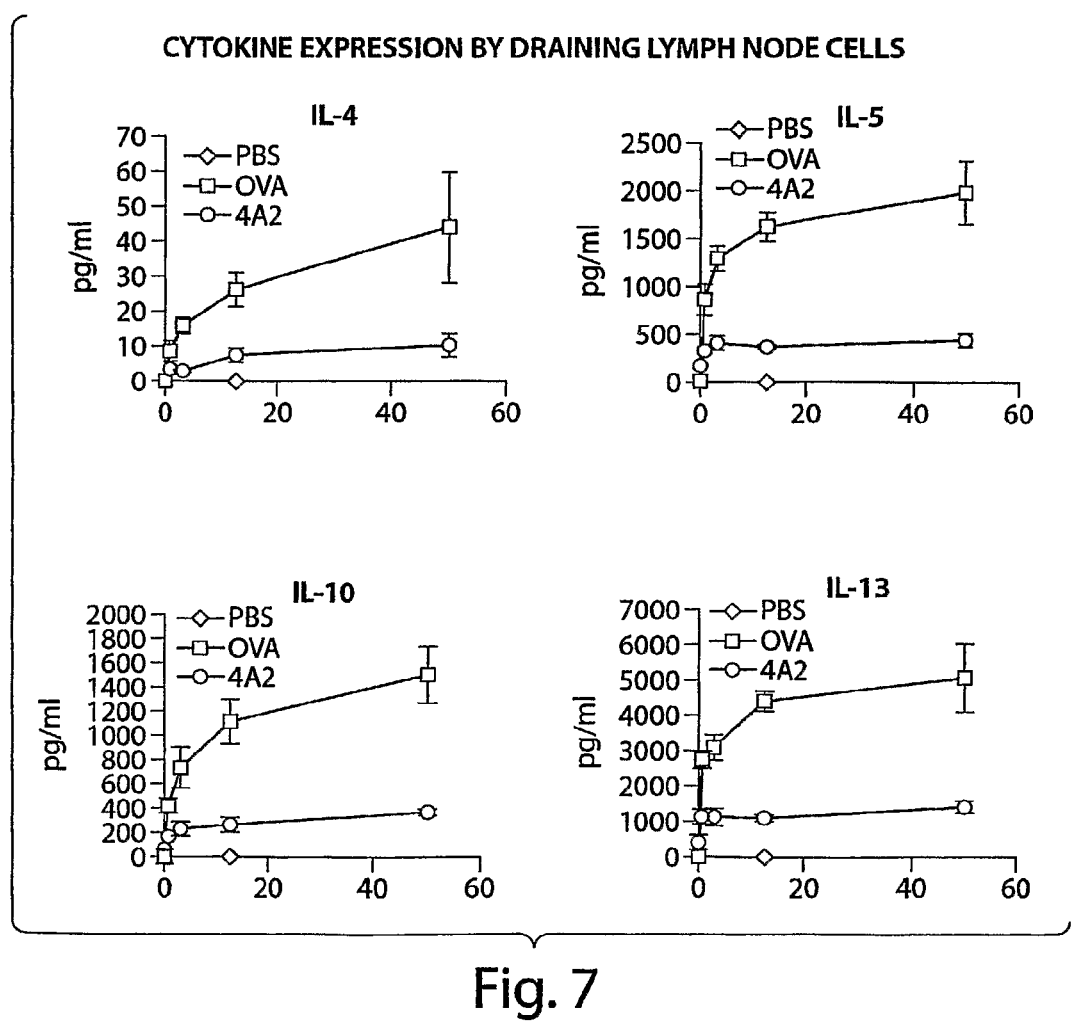
FIG. 7 is a graph showing the response of draining (bronchial) lymph node cells to stimulation ex vivo with the OVA antigen and treatment with 4A2. LN were harvested after OVA aerosol challenge, and then cultured with OVA ex vivo. Supernatants were taken from these cultures and analyzed for Th2 cytokines (IL-4, IL-5, IL-10 and IL-13) production. Y-axis is picograms/ml.

Treatment with the anti-Ig domain mAb 4A2 resulted in a pronounced reduction in eosinophil and lymphocyte influx into the BAL after sensitization with OVA and nebulization treatment (FIG. 6). The average decrease in eosinophil percentage in BAL was 84% compared to control (p<0.0001, test of mean equivalence) and the average decrease in lymphocyte percentage was 90% compared to control (p<0.001, test of mean equivalence). When the bronchial lymph node cells were restimulated with OVA ex vivo there was a dramatic decrease in the production of Th2 cytokines including IL-4, IL-5, IL-10, and IL-13 (FIG. 7). Therefore treatment with mAb 4A2 reduced lung inflammation and the production of cytokines associated with asthma responses.

Figure 8:
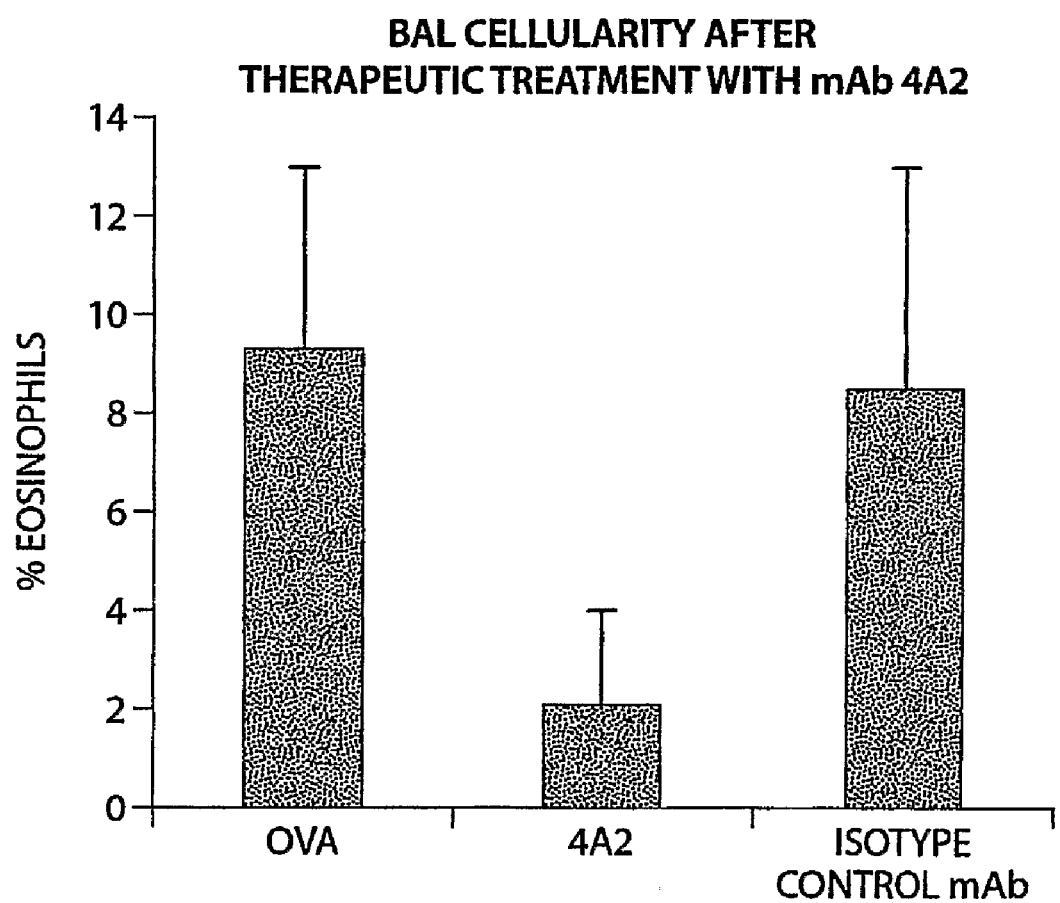
FIG. 8 is a graph showing the percent of eosinophils (y axis) present in bronchial lavage fluid (BAL) after aerosol challenge with OVA and therapeutic treatment with 4A2.

To further characterize the clinical efficacy of mAb 4A2, a therapeutic dosing experiment was performed. In this model, the mice were immunized to develop sensitivity to the OVA antigen, without any mAb treatment being given. The mice were then rested for 3 weeks, again without any treatment, and then dosed with 4A2 mAb the day prior to the first of 3 sessions of nebulization with 1% OVA. The dosing with mAb was repeated prior to the second session. This treatment protocol resulted in the reduction of lung inflammation as measured by the influx of eosinophils into the BAL (FIG. 8). The percent of eosinophils was reduced an average of 70% (p<0.001, test of mean equivalence). Therefore mAb 4A2 was efficacious in both a prophylactic and therapeutic dosing regimen in the OVA-induced lung inflammation model. This suggests that the epitope recognized by 4A2 is a therapeutically relevant target for the treatment of Th2 mediated disorders.

Other anti-KIM-1 mAbs were also demonstrated to have therapeutic activity in the OVA-induced lung inflammation model, including, for example, mAb 2A7 and mAb 2B3. mAb 2A7 was shown to compete with 4A2 for binding to immobilized KIM-1 in a Biocore® assay, suggesting they have shared or overlapping epitopes.

Example 4

Effect of KIM-1 Antibodies on the CD4 T Cell Response to Antigen

The activity of anti-KIM-1 mAbs using the KLH antigen recall assay was evaluated. Mice were treated with anti-KIM-1 mAbs, control mAb, or PBS, then immunized with KLH and 6 days later the draining LN were excised. LN CD4+ T cells were isolated and restimulated ex vivo with purified OVA in the presence of irradiated whole splenocytes isolated from untreated mice. 48 hours after ex vivo stimulation cellular proliferation and cytokine production was assayed. In this assay several of the anti-KIM-1 mAbs had a marked effect. mAb 1H8 dramatically increased T cell proliferation in response to KLH challenge ex vivo. In contrast mAb 3A2 reduced T cell proliferation in the assay. Cytokines produced in the cultures from cells treated with mAb 1H8 were measured. Treated cultures were found to contain more IFN-gamma and TH2-associated cytokines that controls. In contrast levels of TNF and IL-2 were similar to controls.

This data indicates that 1H8 can reduce the pathogenic Th1 response. This data also indicates that 1H8 and other antibodies that bind to the KIM-1 region as defined herein for 1H8 can act as an adjuvant by increasing the immune response. The invention also covers methods of increasing the immune response, e.g., to increase the effectiveness of a vaccine. Such adjuvancy can also have use in vaccination, immunodeficiency, and anti-tumor immunity.

1H8 binds KIM-1 ECD of the Balb/C sequence but not the Dba/2 sequence in Western blots. This indicates that the antibody binds to the alternatively spliced mouse allelic variant containing the sequence EPTTFCPRETTAEVTGIPSHTPT (SEQ ID NO:2). This sequence corresponds to the sequence VATSPSSPQPAETUPTTLQGAIRREPTSSPLYSYTT of human KIM-1 (amino acids 200-235 of SEQ ID NO:1).

Example 5

Characterization of mAb 3A2

Because 3A2 mAb had a therapeutic effect in the OVA model, its binding to KIM-1 was characterized in more detail.

Figure 5:
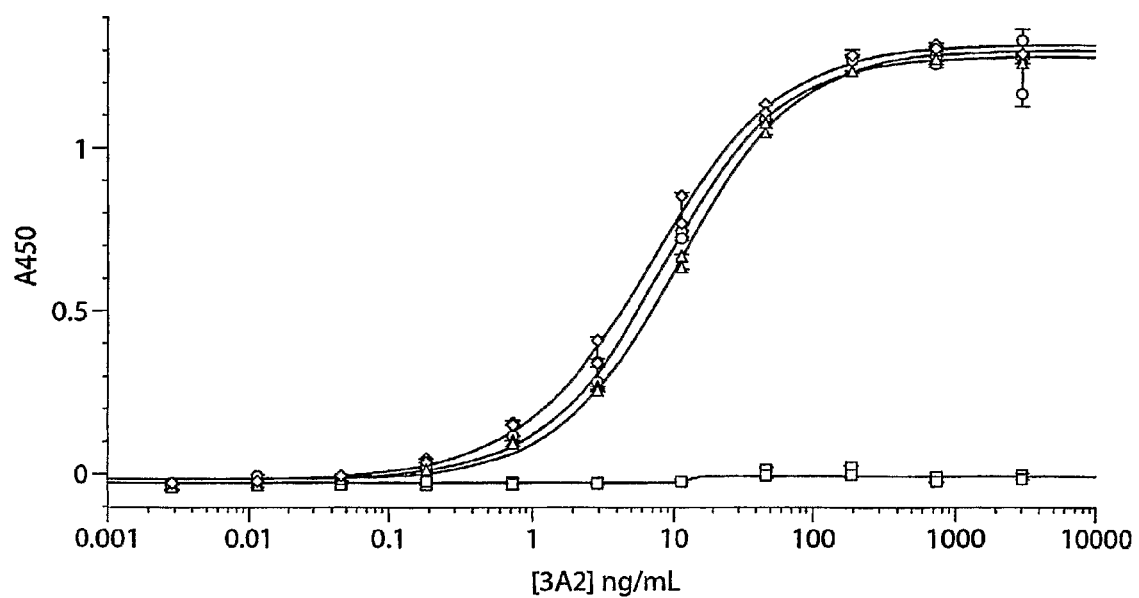
FIG. 5 shows binding curves generated for the interaction of 3A2 with the immobilized proteins. MAb 3A2 bound equivalently to mKIM-1-ECD-Fc (circles), mKIM-1-137-216-Fc (triangles), and mKIM-1-196-216-Fc (diamonds), but failed to bind to mKIM-1-IgV-Fc (squares).

Various purified proteins were used in an ELISA assay to determine the epitope of mAb 3A2 (Table 2). Full binding curves were generated for the interaction of 3A2 with the immobilized proteins (FIG. 5). MAb 3A2 bound equivalently to the following mouse proteins: murine KIM-1 extracellular domain (KIM-1-ECD-1-216), mKIM-1-137-216 and mKIM-1-196-216-Fc. In contrast, mAb 3A2 failed to bind to the mKIM-1-IgV domain alone, which is lacking the entire mucin and stalk domain. This data shows that the epitope for 3A2 resides within the 21 amino acid residues 196 to 216 from mKIM-1, which maps to a portion of the stalk region of KIM-1. This epitope equates to residues 247-272 of human KIM-1 as shown in FIG. 1.

TABLE 2

| DOMAIN | SEQUENCE | 3A2 BINDING |
| --- | --- | --- |
| mKIM-1-ECD (1-216) | SYVEVKGVVGHPVTLPCTYSTYRGITT TCWGRGQCPSSACQNTLIWTNGHRVTY QKSSRYNLKGHISEGDVSLTIENSVES DSGLYCCRVEIPGWFNDQKVTFSLQVK PEIPTRPPTRPTTTRPTATGRPTTIST RSTHVPTSIRVSTSTPPTSTHTWTHKP EPTTFCPHETTAEVTGIPSHTPTDWNG TATSSGDTWSNHTEAIPPGKPQKNPTK (underlined region is encoded by alternatively spliced exon) | yes |
| mKIM-1-IgV (1-109) | SYVEVKGVVGHPVTLPCTYSTYRGITT TCWGRGQCPSSACQNTLIWTNGHRVTY QKSSRYNLKGHISEDGDVSLTIENSVE SDSGLYCCRVEIPGWFNDQKVTFSLQV KP | no |
| mKIM-1-137-216 (137-216) | STHVPTSIRVSTSTPPTSTHTWTHKPE PTTFCPHETTAEVTGIPSHTPTDWNGT ATSSGDTWSNHTEAIPPGKPQKNPTK | yes |
| mKIM-1-196-216 (196-216) | DTWSNHTEAIPPGKPQKNPTK | yes |

Because the stalk region that includes amino acids 196 to 216 of mouse KIM-1 (corresponding to amino acids 247-272 of human KIM-1) contains N-glycosylation sites, it was of interest to determine if a sugar moiety bound to an N-glycosylation site was required for binding of 3A2. Western blot analysis of glycosylated and deglycosylated KIM-1-196-2,6-Fc was performed (FIG. 2). This analysis showed that deglycosylation did not impact the ability of 3A2 to bind to KIM-1-196-2,6-Fc. Therefore a sugar moiety is not required for 3A2 to recognize its epitope.

To determine if 3A2 inhibits shedding of KIM-1 from the cell surface, E293 cells transfected with KIM-1 were treated with 5 ug/mL 3A2, 25 ug/mL 3A2 or no 3A2 (control). Supernatants from both sets of 3A2-treated cells showed no difference in KIM-1 staining from control when run on Western blot probed with biotinylated 1H8 antibody. This suggests that 3A2 does not preventing shedding of KIM-1.

Example 6

Characterization of the 4A2 mAb

Figure 9:
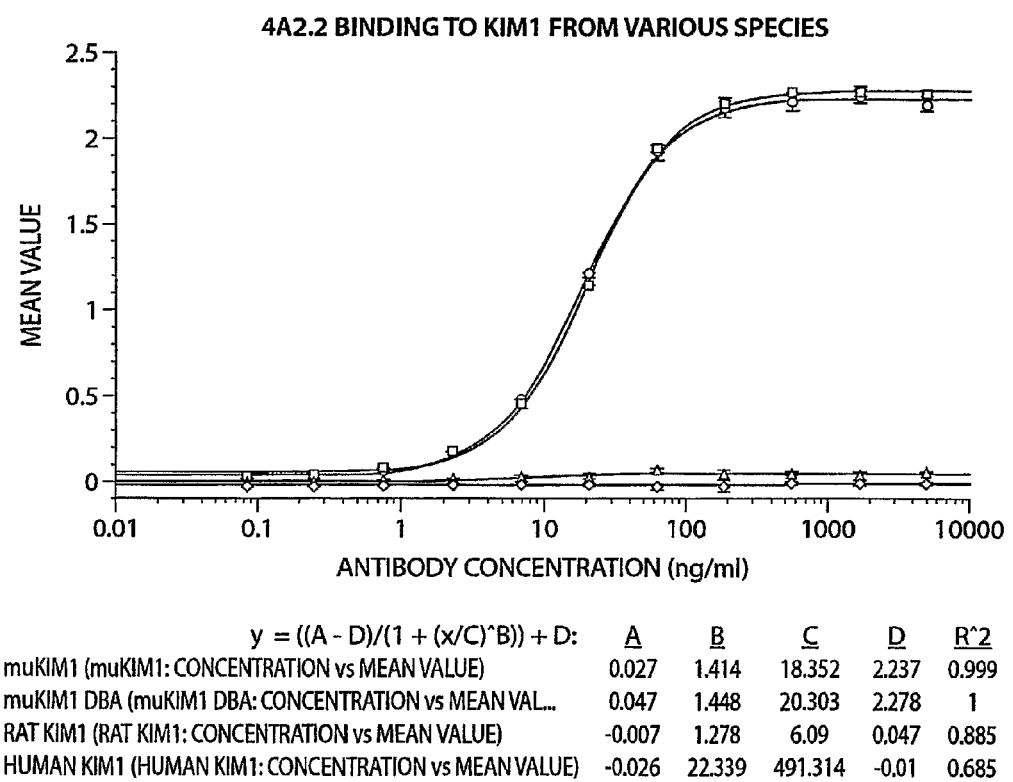
FIG. 9 shows the binding curve of mAb 4A2 to purified KIM-1 proteins.

Using ELISA and Biacore analyses it was determined that mAb 4A2 recognized the Ig-domain of murine KIM-1 (FIG. 9, Table 1). To further characterize the epitope recognized by mAb 4A2, a recombinant murine KIM-1 IgV-human IgG1 Fc fusion, alone and in complex with 4A2, was digested with TPCK trypsin. A band of 8 kDa was generated from KIM-1 alone and is not generated when 4A2 is bound. This indicates that binding of 4A2 to KIM-1 blocks access of trypsin to the cleavage site required to generate this band. Digestion of the 8 Kda band under non-reducing conditions revealed that 4A2 protects a fragment corresponding to human KIM-1 sequence GVYCCRVEHRGWFNDMKITVSLEIVPP (amino acids 81-107 of SEQ ID NO:1). Thus, the 4A2 antibody protects a TPCK trypsin site at least partly within, or overlapping amino acids 81-107 of SEQ ID NO:1.

The same TPCK tryptic digest experiment was performed with 2A7 and a band of approximately the same size was obtained. The band was not obtained when the same experiment was performed with 1H9 (a non-efficacious mAb in the asthma model that also binds to the Ig domain), indicating that the epitope tracks with efficacy in asthma.

The specification is most thoroughly understood in light of the teachings of the references cited within the specification.

The embodiments within the specification provide an illustration of embodiments of the invention and should not be construed to limit the scope of the invention. The skilled artisan readily recognizes that many other embodiments are encompassed by the invention. All publications, patents, and biological sequences cited in this disclosure are incorporated by reference in their entirety. To the extent the material incorporated by reference contradicts or is inconsistent with the present specification, the present specification will supersede any such material. The citation of any references herein is not an admission that such references are prior art to the present invention.

Unless otherwise indicated, all numbers expressing quantities of ingredients, cell culture, treatment conditions, and so forth used in the specification, including claims, are to be understood as being modified in all instances by the term "about." Accordingly, unless otherwise indicated to the contrary, the numerical parameters are approximations and may vary depending upon the desired properties sought to be obtained by the present invention. Unless otherwise indicated, the term "at least" preceding a series of elements is to be understood to refer to every element in the series. Those skilled in the art will recognize, or be able to ascertain using no more than routine experimentation, many equivalents to the specific embodiments of the invention described herein. Such equivalents are intended to be encompassed by the following claims.

---

We claim:

1. A method of treating a Th2-mediated disorder, the method comprising administering to a mammal having a Th2-mediated disorder an antibody, or antigen-binding fragment thereof, that binds the sialic acid binding motif of KIM-1 at an epitope contained within amino acids 81-107 of SEQ ID NO:1.

2. The method of claim 1, wherein the antibody or antigen-binding fragment thereof protects a TPCK trypsin site within amino acids 81-107 of SEQ ID NO:1.

3. The method of claim 1, wherein the antibody or antigen-binding fragment thereof interferes with one or more of residues R86, W92, and F93 of SEQ ID NO:1.

4. The method of claim 1, wherein the mammal is a human.

5. The method of claim 1, wherein the disorder is atopy.

6. The method of claim 1, wherein the disorder is asthma.

7. The method of claim 1, wherein the antibody or antigen-binding fragment thereof is a humanized antibody or antigen-binding fragment thereof.

8. The method of claim 1, wherein a full-length antibody is administered.

9. The method of claim 1, wherein an antigen-binding fragment of the antibody is administered.

10. The method of claim 9, wherein the antigen-binding fragment is selected from the group consisting of a single chain antibody, an Fab fragment, an F(ab')2 fragment, an Fd fragment, an Fv fragment, and a dAb fragment.

11. The method of claim 1, wherein the antibody or antigen-binding fragment thereof is administered in combination with a second therapeutic agent for the disorder.

12. The method of claim 1, wherein the antibody or antigen-binding fragment thereof is administered at a dosage between 0.05 and 20 mg/kg.

13. The method of claim 6, wherein the asthma is allergic asthma.

14. The method of claim 1, wherein the antibody or antigen-binding fragment thereof is a fully human monospecific antibody or antigen-binding fragment thereof.

15. The method of claim 4, wherein the disorder is atopy.

16. The method of claim 4, wherein the disorder is asthma.

17. The method of claim 16, wherein the asthma is allergic asthma.

18. The method of claim 4, wherein the antibody or antigen-binding fragment thereof is a humanized antibody or antigen-binding fragment thereof.

19. The method of claim 4, wherein the antibody or antigen-binding fragment thereof is a fully human monospecific antibody or antigen-binding fragment thereof.

20. The method of claim 4, wherein a full-length antibody is administered.

21. The method of claim 4, wherein an antigen-binding fragment of the antibody is administered.

22. The method of claim 21, wherein the antigen-binding fragment is selected from the group consisting of a single chain antibody, an Fab fragment, an F(ab')2 fragment, an Fd fragment, an Fv fragment, and a dAb fragment.

23. The method of claim 15, wherein the antibody or antigen-binding fragment thereof is a humanized antibody or antigen-binding fragment thereof.

24. The method of claim 15, wherein the antibody or antigen-binding fragment thereof is a fully human monospecific antibody or antigen-binding fragment thereof.

25. The method of claim 15, wherein a full-length antibody is administered.

26. The method of claim 15, wherein an antigen-binding fragment of the antibody is administered.

27. The method of claim 26, wherein the antigen-binding fragment is selected from the group consisting of a single chain antibody, an Fab fragment, an F(ab')2 fragment, an Fd fragment, an Fv fragment, and a dAb fragment.

28. The method of claim 16, wherein the antibody or antigen-binding fragment thereof is a humanized antibody or antigen-binding fragment thereof.

29. The method of claim 16, wherein the antibody or antigen-binding fragment thereof is a fully human monospecific antibody or antigen-binding fragment thereof.

30. The method of claim 16, wherein a full-length antibody is administered.

31. The method of claim 16, wherein an antigen-binding fragment of the antibody is administered.

32. The method of claim 31, wherein the antigen-binding fragment is selected from the group consisting of a single chain antibody, an Fab fragment, an F(ab')2 fragment, an Fd fragment, an Fv fragment, and a dAb fragment.

33. The method of claim 17, wherein the antibody or antigen-binding fragment thereof is a humanized antibody or antigen-binding fragment thereof.

34. The method of claim 17, wherein the antibody or antigen-binding fragment thereof is a fully human monospecific antibody or antigen-binding fragment thereof.

35. The method of claim 17, wherein a full-length antibody is administered.

36. The method of claim 17, wherein an antigen-binding fragment of the antibody is administered.

37. The method of claim 36, wherein the antigen-binding fragment is selected from the group consisting of a single chain antibody, an Fab fragment, an F(ab')2 fragment, an Fd fragment, an Fv fragment, and a dAb fragment.

* * * * *

UNITED STATES PATENT AND TRADEMARK OFFICE
CERTIFICATE OF CORRECTION

| | | |
|---|---|---|
| PATENT NO. | : 8,206,705 B2 | Page 1 of 1 |
| APPLICATION NO. | : 11/817638 | |
| DATED | : June 26, 2012 | |
| INVENTOR(S) | : Paul Rennart | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 661 days.

Signed and Sealed this

Fourth Day of September, 2012

David J. Kappos
*Director of the United States Patent and Trademark Office*